US009566772B2

(12) United States Patent
Lynn et al.

(10) Patent No.: US 9,566,772 B2
(45) Date of Patent: Feb. 14, 2017

(54) METHODS FOR MAKING A PLURALITY OF FILTER ASSEMBLIES

(71) Applicant: Fenwal, Inc., Lake Zurich, IL (US)

(72) Inventors: Daniel Lynn, Spring Grove, IL (US); Tat Mui, Chicago, IL (US); Andres Pasko, Genoa, WI (US); Mark Jones, Libertyville, IL (US); Kwang Suk Kim, Palatine, IL (US); Walter Timothy Watts, Arlington Heights, IL (US); Dennis Clyde Berry, Woodstock, IL (US); James Darren Roxas, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 732 days.

(21) Appl. No.: 13/685,068

(22) Filed: Nov. 26, 2012

(65) Prior Publication Data
US 2013/0092319 A1 Apr. 18, 2013

Related U.S. Application Data

(62) Division of application No. 12/569,551, filed on Sep. 29, 2009, now abandoned.
(Continued)

(51) Int. Cl.
*B32B 37/10* (2006.01)
*A61M 1/36* (2006.01)

(52) U.S. Cl.
CPC ............ *B32B 37/10* (2013.01); *A61M 1/3633* (2013.01); *A61M 1/3636* (2014.02); *Y10T 156/1054* (2015.01); *Y10T 156/1084* (2015.01)

(58) Field of Classification Search
CPC ... B32B 37/10; A61M 1/3636; A61M 1/3635; A61M 1/3633; A61M 1/3627; A61M 1/3621; A61M 1/360209; A61M 1/02; Y10T 156/1084; Y10T 156/1052; Y10T 156/10; B01D 29/012; B01D 29/01111; B01D 29/111623; B01D 29/1607; B01D 29/16; B01D 29/14; B29C 65/04
(Continued)

(56) References Cited

U.S. PATENT DOCUMENTS 3,556,302 A 1/1971 Agranat
4,113,627 A 9/1978 Leason
(Continued)

FOREIGN PATENT DOCUMENTS

WO WO 0156679 A1 8/2001
WO WO 0191880 A1 12/2001

OTHER PUBLICATIONS

Office Action for U.S. Appl. No. 12/569,551, dated Mar. 14, 2012.
(Continued)

*Primary Examiner* — David C Mellon
*Assistant Examiner* — Liam Royce
(74) *Attorney, Agent, or Firm* — Cook Alex Ltd.

(57) ABSTRACT

A method for manufacturing a plurality of filter assemblies is provided that includes providing first and second housing sheets and positioning a filtration medium therebetween. Heat and pressure are applied to form first, second, and peripheral seals of at least two filter assemblies at the same time. Each second seal is positioned outboard of the associated first seal with a non-seal area therebetween, while each peripheral seal is positioned outboard of the associated second seal. The first seal commingles the housing sheets and the filtration medium, while the peripheral seal and the periphery of the second seal commingle only the housing sheets. The peripheral seal may include a tear seal to enable separation of a plurality of adjacent filter assemblies.

14 Claims, 8 Drawing Sheets

Related U.S. Application Data

(60) Provisional application No. 61/101,034, filed on Sep. 29, 2008, provisional application No. 61/101,484, filed on Sep. 30, 2008.

(58) Field of Classification Search
USPC .......... 210/435, 232; 156/60, 166, 251, 250, 156/290, 581, 580, 349; 604/408, 403
See application file for complete search history.

(56) References Cited

U.S. PATENT DOCUMENTS

| | | | |
|---|---|---|---|
| 4,220,489 A * | 9/1980 | Coplan et al. | ............... 156/73.6 |
| 4,302,333 A | 11/1981 | Cosack et al. | |
| 4,676,051 A * | 6/1987 | Hoskinson | .......... B29C 66/8221 |
| | | | 53/374.9 |
| 4,831,664 A | 5/1989 | Suda | |
| 5,507,904 A | 4/1996 | Fisher et al. | |
| 5,733,406 A * | 3/1998 | Knight | ........................ 156/359 |
| 6,367,634 B1 | 4/2002 | Lynn et al. | |
| 6,422,397 B1 | 7/2002 | Lynn et al. | |
| 6,745,902 B2 | 6/2004 | Lynn et al. | |
| 7,278,541 B2 | 10/2007 | Breillatt, Jr. et al. | |
| 7,332,096 B2 | 2/2008 | Blickhan | |
| 7,353,956 B2 | 4/2008 | Lynn et al. | |
| 8,857,627 B2 * | 10/2014 | Yokomizo | ............... A61M 1/02 |
| | | | 210/435 |
| 2001/0037078 A1 * | 11/2001 | Lynn et al. | ................... 604/6.09 |
| 2002/0148764 A1 * | 10/2002 | Lynn | ................... A61M 1/0209 |
| | | | 210/257.1 |
| 2003/0000886 A1 * | 1/2003 | Breillatt | ............... A61M 1/3633 |
| | | | 210/435 |
| 2003/0106799 A1 * | 6/2003 | Covington et al. | ........... 204/600 |
| 2003/0209479 A1 | 11/2003 | Lynn et al. | |

OTHER PUBLICATIONS

Office Action for U.S. Appl. No. 12/569,551, dated Aug. 29, 2012.

* cited by examiner

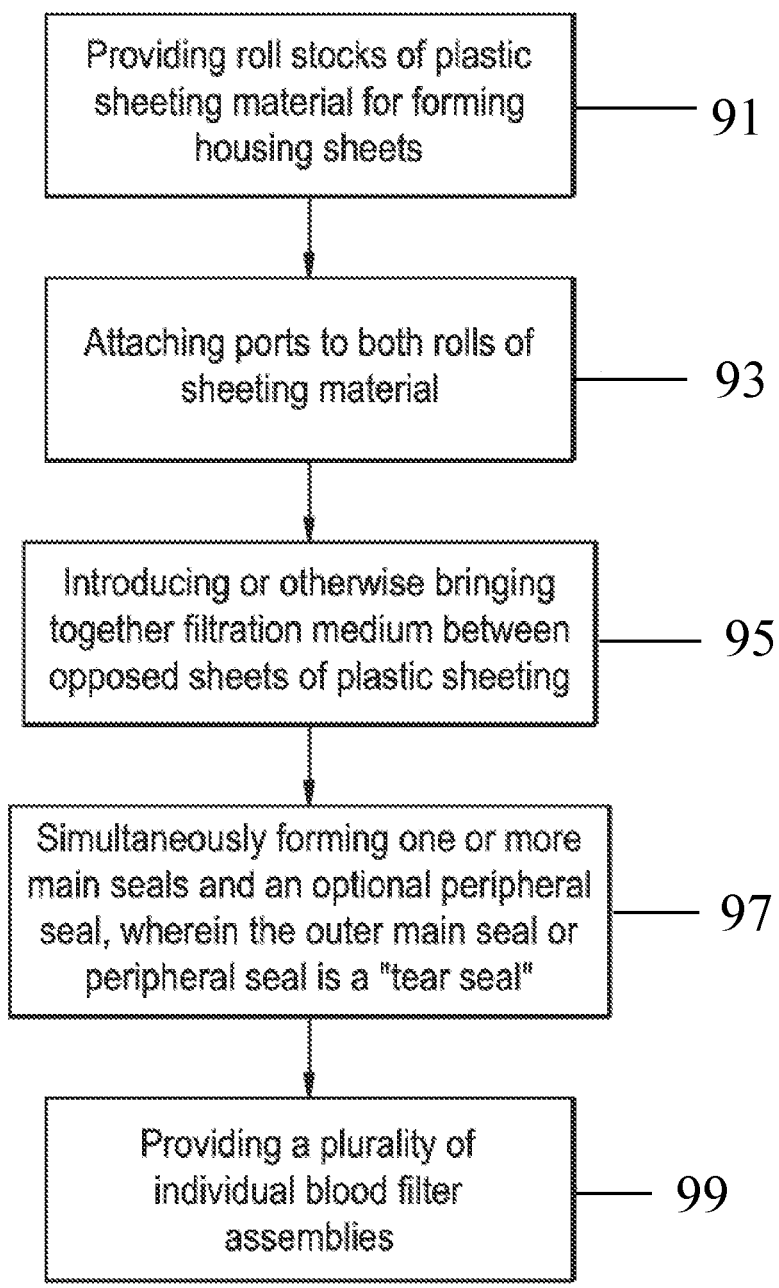

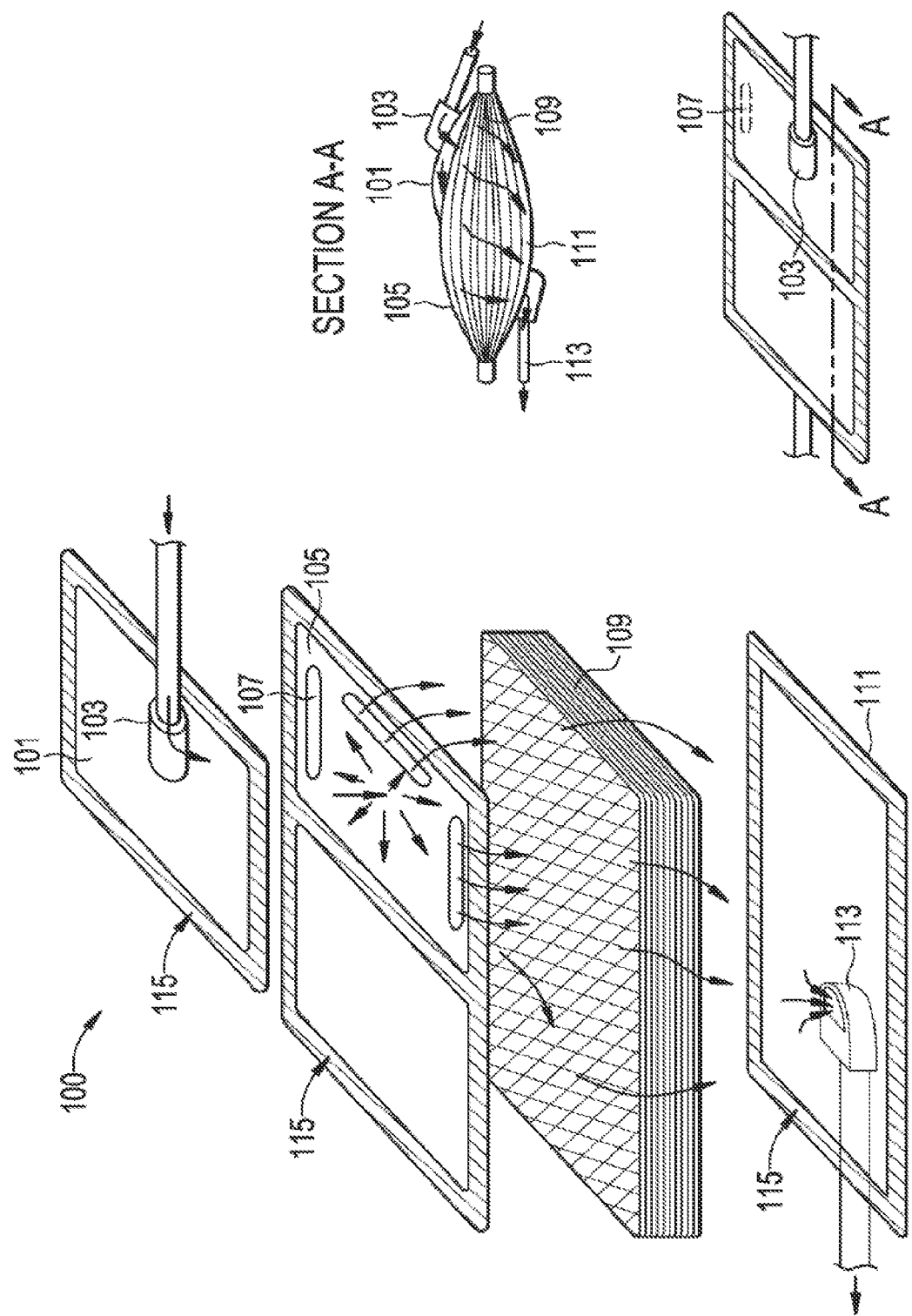

METHODS FOR MAKING A PLURALITY OF FILTER ASSEMBLIES

CROSS-REFERENCE TO RELATED APPLICATIONS

The present application is a divisional application of U.S. patent application Ser. No. 12/569,551, filed on Sep. 29, 2009, and claims the benefit of priority to U.S. Provisional Patent Application No. 61/101,034, filed on Sep. 29, 2008, entitled "FLEXIBLE HOUSING FILTER AND METHODS FOR MAKING SUCH FILTER", and U.S. Provisional Patent Application No. 61/101,484, filed on Sep. 30, 2008, entitled "FLEXIBLE HOUSING FILTER AND METHODS FOR MAKING SUCH FILTER", each of which is herein incorporated by reference in its entirety.

FIELD OF THE INVENTION

The present disclosure generally relates to methods of manufacturing filters used in the collection and processing of blood and blood components or other biological fluid. More particularly, the present disclosure relates to methods of manufacturing a plurality of such filters.

BACKGROUND

Using various manual and automated systems and methods, whole blood is collected and separated into its clinical components (typically red blood cells, platelets, and plasma). The collected components are typically individually stored and used to treat a variety of specific conditions and diseased states.

Before transfusing the collected blood components to a recipient in need of the component, or before subjecting blood components to treatment (such as but not limited to pathogen inactivation), it is often desirable to minimize the presence of impurities or other materials that may cause undesired side effects in the recipient. For example, because of possible reactions, it is generally considered desirable to reduce the number of leukocytes in blood components before storage, or at least before transfusion (i.e., "leukoreduction").

Filters are widely used to accomplish leuko-reduction in blood products today (e.g., warm and cold filtration of leukocytes from whole blood, red cells, and/or platelet products). Filters typically include a filter media disposed between mating walls of a filter housing. Inlet and outlet ports associated with the housing provide flow to and from the interior of the filter. The walls of the housing may be made of a rigid, typically plastic, material, although filters including soft housings are also known. Soft housing filters provide the advantage of being able to withstand handling and centrifuging without breakage of the filter. Examples of soft housing filters are disclosed in U.S. Pat. No. 6,367,634 issued Apr. 9, 2002; U.S. Pat. No. 6,422,397 issued Jul. 23, 2002; U.S. Pat. No. 6,745,902 issued Jul. 8, 2004; U.S. Pat. No. 7,353,956 issued Apr. 8, 2007; U.S. Pat. No. 7,332,096 issued Feb. 19, 2008; U.S. Pat. No. 7,278,541 issued Oct. 9, 2007; and U.S. application Ser. No. 10/275,805 filed Mar. 10, 2003, all of which are incorporated by reference herein. Due to the importance of filtering blood or blood components, there exists an ongoing desire to improve the construction, performance, and manufacturability of blood filters.

SUMMARY

Certain examples provide systems, methods, and articles of manufacture for blood product filtering.

An example method for manufacturing a plurality of filter assemblies is provided that includes the steps of providing a first housing sheet and a second housing sheet from housing sheet roll stocks. The method includes locating the filtration medium between the first housing sheet and the second housing sheet. The method includes applying heat and pressure to form at least one seal that commingles the first and second housing sheets along with the filtration medium, a second seal, outboard of the first seal, that commingles at least the first and second housing sheets, and a peripheral seal that commingles the first and second housing sheets outboard of the second seal. The periphery of the second seal commingles only the first and second housing sheets, with a non-seal area being defined between the first and second seals. The peripheral seal includes a tear seal enabling separation of a plurality of filter assemblies. The first, second, and peripheral seals of one of the filter assemblies are formed at the same time as the first, second, and peripheral seals of another one of the filter assemblies.

Another example method is provided to manufacture a plurality of filter assemblies by providing a first housing sheet and a second housing sheet; associating at least one port with each of the first and second housing sheets; and positioning a filtration medium between said first housing sheet and said second housing sheet. The method includes applying heat and pressure to form a first seal around each port that commingles the first and second housing sheets along with the filtration medium and a second seal around each port, outboard of the first seal, that commingles at least the first and second housing sheets, wherein the periphery of the second seal commingles only the first and second housing sheets. A non-seal area is formed between the first seal and the second seal. A peripheral seal is formed around each port that commingles the first and second housing sheets outboard of each second seal. The first, second, and peripheral seals of one of the filter assemblies are formed at the same time as the first, second, and peripheral seals of another one of the filter assemblies. Adjacent filter assemblies are separated at the peripheral seals.

BRIEF DESCRIPTION OF THE FIGURES

In the course of this description, reference will be made to the accompanying drawings, wherein:

FIG. 9 is a diagrammatic view of one method of manufacturing a blood filter assembly.

FIG. 10 shows an example filter for leuko-reduction of a blood product fluid.

Features, further aspects, and advantages of the present invention will become apparent from the following description of embodiments thereof, by way of example only, with reference to the accompanying drawings. Also, various embodiments of the aspects described in the preceding paragraphs will be apparent from the appended claims, the following description and/or the accompanying drawings. It should be understood, however, that the present invention is not limited to the arrangements and instrumentality shown in the attached drawings.

DETAILED DESCRIPTION OF CERTAIN EMBODIMENTS

It will be seen from the following description that there are several possible variations and embodiments of soft housing filters according to the present disclosure, including, but not limited to, the filter assemblies generally shown in FIGS. 1-4.

Figure 1:
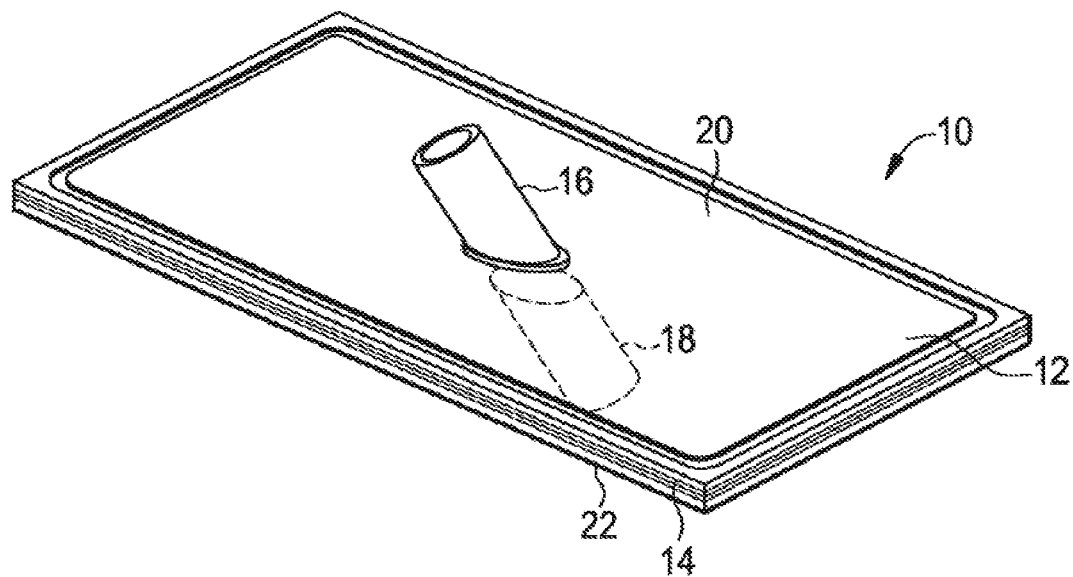
FIG. 1 is an assembled perspective view of a blood filter assembly.

FIG. 1 shows a filter assembly generally designated at 10. The filter assembly 10 is useful in the collection and/or processing of blood, blood components, or other biological fluid in either a manual or automated fashion. In the illustrated embodiments, the blood filter is intended, during use, to selectively remove leukocytes from whole blood or components of whole blood, such as red blood cells, platelets, or plasma.

It will be seen from the following description that there are several possible variations and embodiments of filters and the sealing of the filter media to the flexible walls of the filter according to the present disclosure. Many of the features of the filter of the present disclosure are further shown and described in association with FIGS. 1-5. Moreover, as noted above, soft housing blood filters are described in U.S. Pat. No. 6,367,634 issued Apr. 9, 2002; U.S. Pat. No. 6,422,397 issued Jul. 23, 2002; U.S. Pat. No. 6,745,902 issued Jul. 8, 2004; U.S. Pat. No. 7,353,956 issued Apr. 8, 2007; U.S. Pat. No. 7,332,096 issued Feb. 19, 2008; U.S. Pat. No. 7,278,541 issued Oct. 9, 2007; and U.S. application Ser. No. 10/275,805 filed Mar. 10, 2003, (all of which have previously been incorporated by reference in their entireties). Thus, the materials and components, filter media and construction described in the above-identified patents and applications may also apply to the blood filters of the present disclosure.

Common to all of the embodiments described and shown below is a blood or biological fluid filter assembly 10 having a housing 12 with a fluid inlet 16 and a fluid outlet 18. The housing 12 encloses a blood filtration medium 14, as FIG. 1 shows. In one example, the fluid inlet 16 conveys blood from a blood source such as a donor or a container holding the blood or blood component, into the housing for passage through the blood filtration medium 14. The fluid outlet 18 conveys blood from the housing after passage through the blood filtration medium 14 to a collection or other container. The filter, source container and collection container (not shown) may all be part of an integral disposable blood processing set for manual or automated collection systems, as will be known to those of skill in the art.

The filter housing 12 can be made using conventional approved medical grade plastic materials, for example. Such material can be rigid or semi-rigid, in which case the housing 12 can be molded or machined to the desired size and configuration.

As shown in the embodiment illustrated in FIG. 1, the filter housing 12 is made from a flexible plastic material, such as the same material from which the source and/or collection container (e.g., blood storage bag, etc.) is made. The filter assembly 10, being flexible, facilitates handling and reduces the incidence of damage to other plastic components used in association with the filter assembly 10 for a given blood processing procedure. The use of flexible plastic material also enables the use of conventional radio frequency heat sealing technology to seal the filter assembly 10, as will be described in greater detail later.

In the particular embodiment shown in FIG. 1, the housing 12 includes first and second sheets 20 and 22 of medical grade plastic material, such as polyvinyl chloride plasticized with di-2-ethylhexyl-phthalate (PVC-DEHP), citrate ester or other suitable plasticizers. Other medical grade plastic materials can be used that are not PVC and/or are DEHP-free, provided that the material heats and flows when exposed to radio frequency energy.

The filtration medium 14 can be variously constructed, e.g., from porous membrane materials or fibers, depending upon the objectives of filtration and the nature of the blood component or biological fluid being filtered. In the illustrated embodiment, the filtration medium 14 is made from a fibrous material, which is sandwiched between the sheets 20 and 22. The medium 14 can include melt blown or spun bonded synthetic fibers (e.g., nylon or polyester or polypropylene), semi-synthetic fibers, regenerated fibers, or inorganic fibers. In use, the medium 14 removes leukocytes by depth filtration, size exclusion, material affinity or other means known to those of skill in the art.

Figure 2:
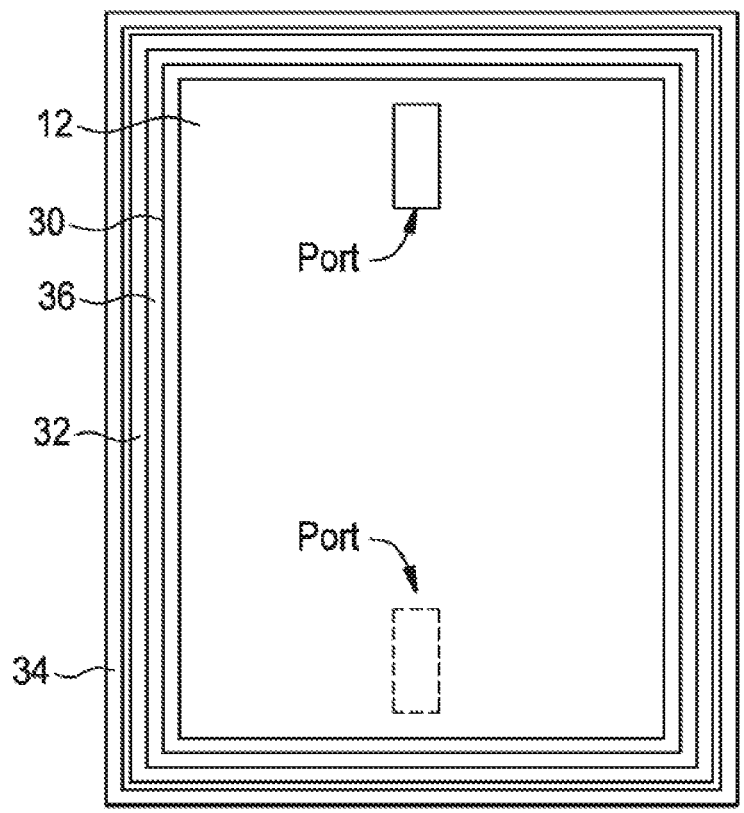
FIG. 2 is a top view of an alternative embodiment of a blood filter assembly.

In one embodiment illustrated in FIG. 2, the seal of the filter assembly includes a unitary, continuous first main seal 30 formed by the application of pressure and radio frequency heating in a single process steps to the two sheets 20 and 22 and the filtration medium 14. The first main seal 30 joins the two sheets 20 and 22 to each other, as well as joins the filtration medium 14 to the two sheets 20 and 22. The first main seal 30 integrates the material of the filtration medium 14 and the material of the plastic sheets 20 and 22, providing a reliable, robust, leak-proof boundary. Since the first main seal 30 is unitary and continuous, the possibility of blood shunting around the periphery of the filtration medium 14 is substantially reduced if not eliminated.

In the illustrated embodiment the seal of the filter assembly also includes a second main seal 32, outboard of the first main seal 30, that can also be formed by the application of pressure and radio frequency heating in a single process step to the two sheets 20 and 22 and the filtration medium 14. Like the first main seal 30, the second main seal 32 integrates the material of the filtration medium 14 and the material of the plastic sheets 20 and 22, providing a reliable, robust, leak-proof boundary. Again, since the second main seal 32 is unitary and continuous, the possibility of blood shunting around the periphery of the filtration medium 14 is substantially reduced if not eliminated.

If desired, a peripheral seal 34, outboard of the first and second main seals 30 and 32, can be formed by radio frequency heating or other sealing means to join the peripheries of the housing sheets 20 and 22. The main seals and the peripheral seal can be formed in sequential heat sealing processes, or preferably in a single heat sealing process.

In an embodiment, a tear seal can be formed adjacent to and/or as part of the peripheral seal 34 to separate a series of filter assemblies 10. Alternative and/or in addition, a die and/or manual cutter can be used to separate a sheet of several sealed filter assemblies into separate filter assembly units 10.

In one embodiment, the preferable width of the first main seal 30 is within a range of about 5/64 of an inch to about 9/32 of an inch, more preferably about 1/8 of an inch. A reduced seal width is believed to minimize the possibility of cracking during centrifugation or flexing of the filter generally, thus maintaining the integrity of the seal. The preferable width of the second main seal 32 is preferably likewise within a range of about 5/64 of an inch to about 9/32 of an inch, more preferably about 1/8 of an inch.

The width of the non seal area 36 between the first main seal 30 and the second main seal 32 is generally within a range of about 1/128 of an inch to about 1/4 of an inch. This overall filter assembly formation allows the filter to maintain flexibility during centrifugation.

Figure 3:
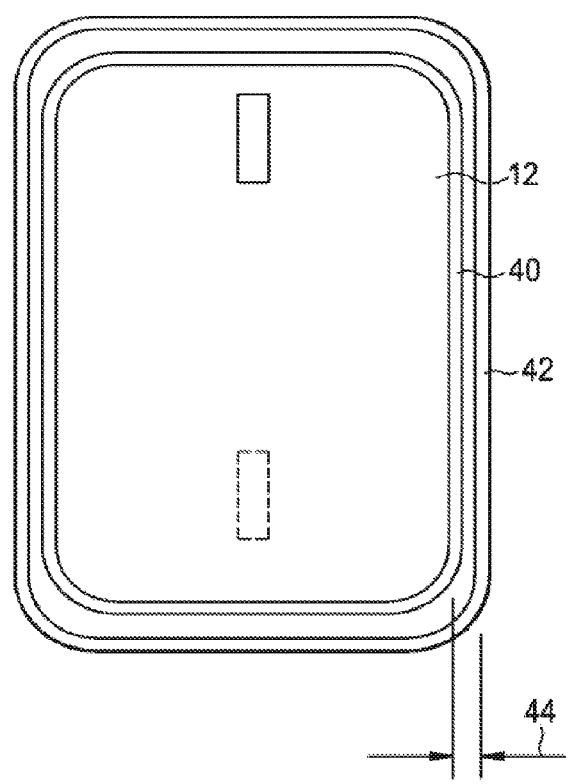
FIG. 3 is a top view of another alternative embodiment of a blood filter assembly.

In another embodiment illustrated in FIG. 3, the seal of the filter assembly includes a unitary, continuous main seal 40 formed by the application of pressure and radio frequency heating in a single process step to the two sheets 20 and 22 and the filtration medium 14. The main seal 40 joins the two sheets 20 and 22 to each other, as well as joins the filtration medium 14 to the two sheets 20 and 22. The main seal 40 integrates the material of the filtration medium 14 and the material of the plastic sheets 20 and 22, providing a reliable, robust, leak-proof boundary. Since the main seal 40 is unitary and continuous, the possibility of blood shunting around the periphery of the filtration medium 14 is substantially reduced or eliminated.

In the illustrated embodiment the seal of the filter assembly also includes a peripheral seal 42, outboard of the main seal 40. The peripheral seal 42 can be formed by radio frequency heating to join the peripheries of the sheets 20 and 22. The main seals and the peripheral seal can be formed in sequential heat sealing processes, or simultaneously in a single heat sealing process.

The width of the non seal area 44 between the main seal 40 and the peripheral seal 42 is generally about 0 to 1 mm. This overall filter formation allows for less material to be used and allows for more efficient centrifugation due to the overall size of the blood filter.

Figure 4:
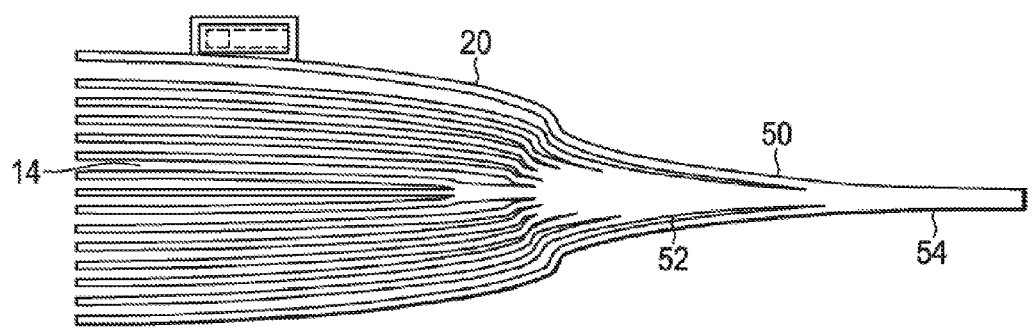
FIG. 4 is a partial cross section view of yet another alternative embodiment of a blood filter assembly.

In yet another embodiment illustrated in FIG. 4, the seal of the filter assembly includes a unitary, continuous seal 50 formed by the application of pressure and radio frequency heating in a single process steps to the two sheets 20 and 22 and the filtration medium 14. The first portion 52 of seal 50 joins the two sheets 20 and 22 to each other, as well as joins the filtration medium 14 to the two sheets 20 and 22. The main seal 38 integrates the material of the filtration medium 14 and the material of the plastic sheets 20 and 22, providing a reliable, robust, leak-proof boundary. Since the first portion 52 of the seal 50 is unitary and continuous, the possibility of blood shunting around the periphery of the filtration medium 14 is substantially reduced or eliminated.

A second portion 54 of the seal 50 joins the peripheries of the sheets 20 and 22. In the illustrated embodiment, there is no gap in the seal between the first and second portions 52 and 54 of the seal 50. This formation allows a seal that prevents blood shunting and creates a hermetic seal to be formed in a single step.

Figure 5:
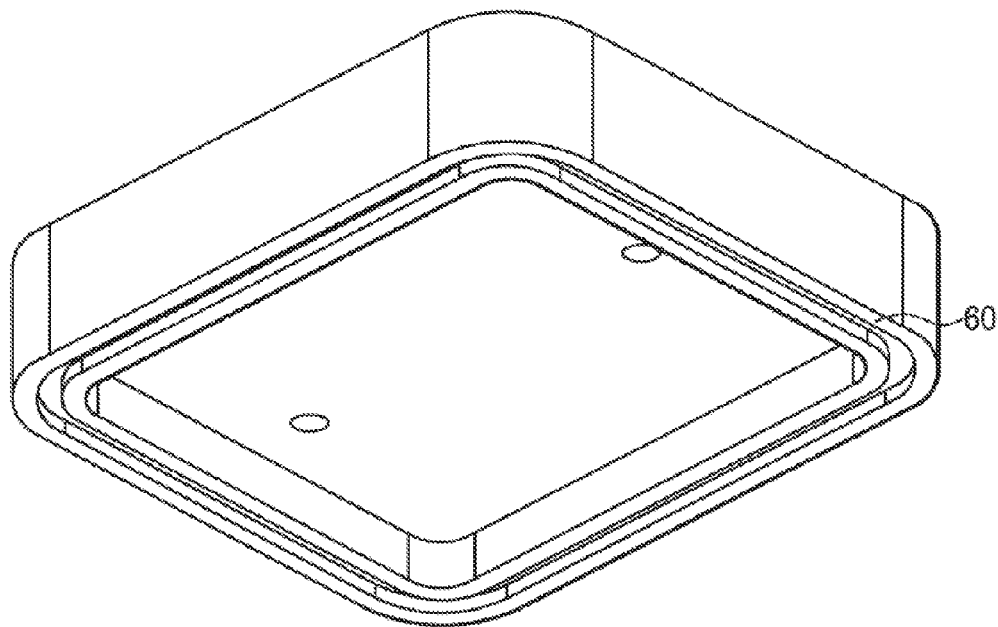
FIG. 5 is a perspective view of one embodiment of a die that forms a seal of the blood filter assembly.

The seals discussed above that seal the filter housing elements with the filtration medium may be formed using conventional heat sealing technologies, e.g., radio frequency (RF). For example, the first and second housing sheets 20 and 22, the filtration medium 14, are placed between a pair of opposed dies. One embodiment of half of the die is illustrated in FIG. 5. When moved together, the opposed dies sandwich the filter assembly 10 and apply pressure to press the sheets and media of the filter assembly 10 together. As the dies apply pressure along the seal location, RF energy is applied through the dies. The combination of RF energy and pressure softens the plastic material of the first and second housing sheets 20 and 22. The applied pressure causes the heat softened material of the sheets 20, 22 to penetrate the interstices of the filtration medium 14, creating an interior matrix of sheet material commingled with filtration medium material. Within the matrix, the filtration medium melts, creating a composite seal.

The dies used to form the seal may provide a seal of selected thickness. In one embodiment, particularly one where the filter includes a first and second main seal, a main seal and peripheral seal, or a first and second main seal and a peripheral seal, the thickness of each seal may be substantially identical or, if desired, different.

Figure 6:
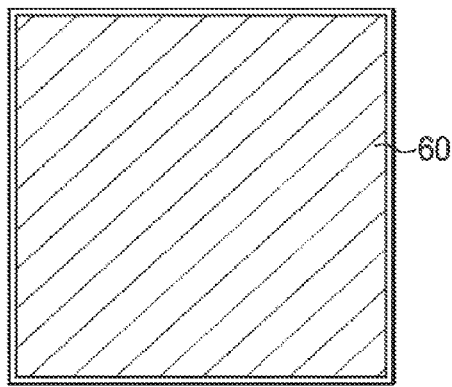
FIG. 6 is a side view of one configuration of the ridge of the die shown in FIG. 5.
Figure 7:
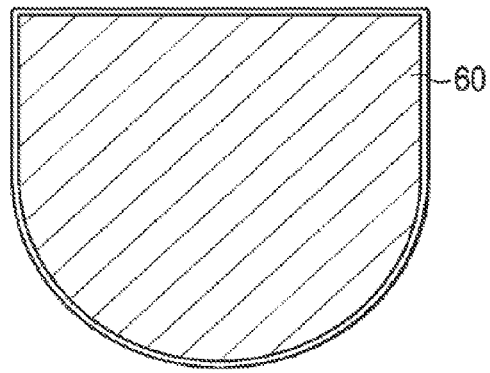
FIG. 7 is a side view of one configuration of the ridge of the die shown in FIG. 5.

The die illustrated in FIG. 5 has a ridge 60 along which the seal is formed. Conventional ridge 60 has a rectangular shape as illustrated in FIG. 6. An alternative configuration of ridge 60 is illustrated in FIG. 7. The seal formed by ridge 60 as illustrated in FIG. 7 has an other than rectangular shape, such as a general arch configuration with a selected radius.

As mentioned above, each of the illustrated embodiments include a fluid inlet 16 and a fluid outlet 18. The inlet and outlet 16 and 18 include tubes made of medical grade plastic material, like plasticized PVC. As FIG. 1 shows, the inlet and outlet 16 and 18 can be can be attached and sealed to each housing sheet 20 and 22 in a separate assembly process before the seal is formed, in the manner shown in Fischer et al. U.S. Pat. No. 5,507,904, which is hereby incorporated by reference in its entirety. Alternatively, the inlet and outlet 16 and 18 can include separately molded parts that are heat sealed by radio frequency energy over or under a hole formed in the sheets 20 and 22. Still alternatively, inlet and outlet 16 and 18 can be located between the sheets of the housing and sealed with the peripheries of the sheets as shown in U.S. Pat. No. 7,353,956 issued Apr. 8, 2008 which has previously been incorporated by reference in its entirety.

Figure 8:
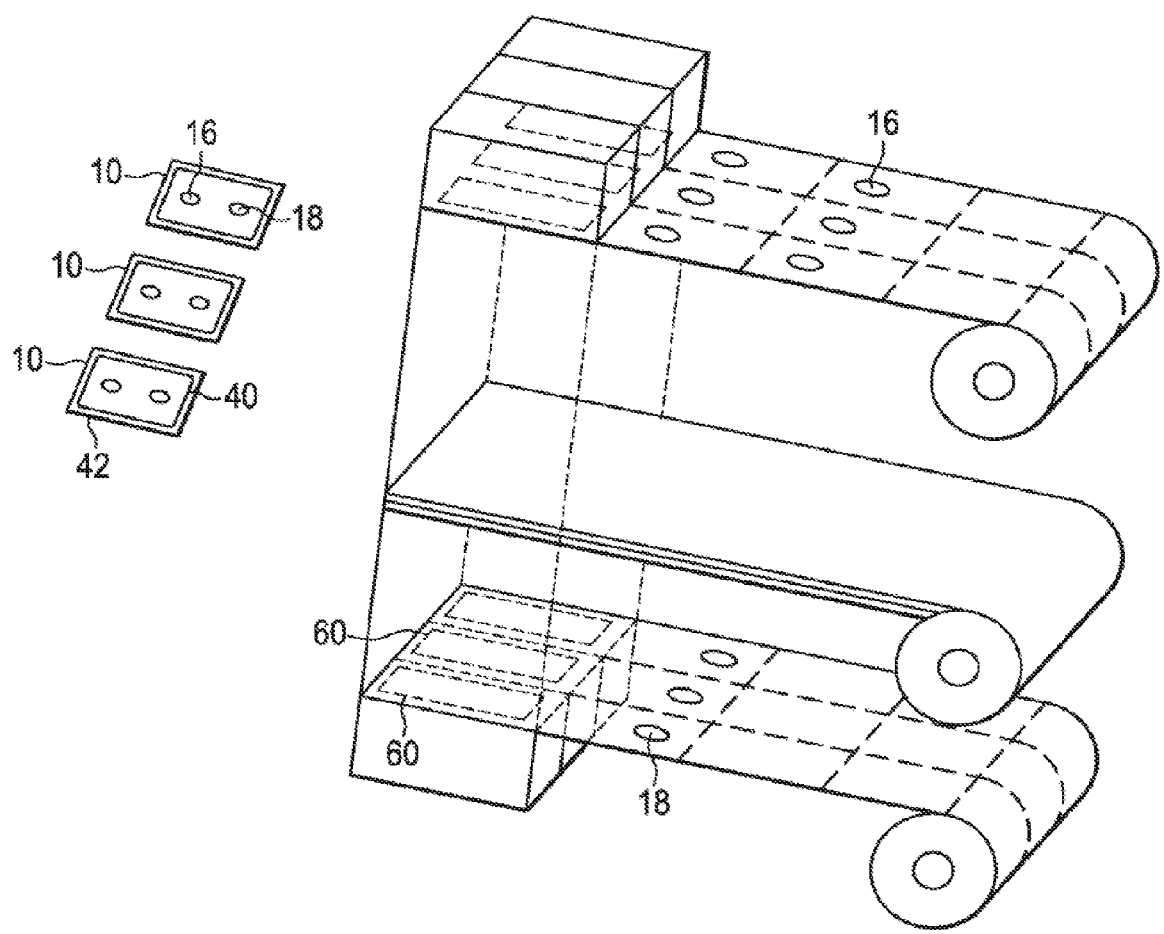
FIG. 8 is a perspective diagrammatic view showing a pre-assembled form of the blood filter assembly being assembled from continuous roll stock.

Filters 10 described herein may be manufactured in accordance with the following method as shown generally in FIG. 8. A roll stock of plastic flexible material (e.g., PVC) for the first and second housing sheets 20 and 22 is provided. Inlet and outlet ports 16 and 18 and preferably a plurality of inlet and outlet ports can be attached and sealed to the roll stock of flexible plastic material in a separate assembly process prior to assembly of the filter. Once ports 16 and 18 have been attached to the plastic sheets of the housing walls, the roll stocks of plastic material are combined with a roll stock of the filtration medium to provide a continuous, layered filter pre-assembly. The pre-assembly is advanced in measured steps between any number of opposed dies (see FIG. 8). Between each step, the opposed dies are moved together, to apply pressure to seal the pre-assembly together in a single step.

As the dies apply pressure, RF energy is applied through the dies. The combination of RF energy and pressure softens the plastic material of the sheets 20 and 22. The applied pressure causes the heat softened material of the sheets 20, 22 to penetrate the interstices of the filtration medium 14, creating an interior matrix of sheet material commingled with filtration medium material. Within the matrix, the filtration medium melts, creating a seal. In an alternative embodiment, the dies can be configured or applied such that as the dies are moved together the filter medium 14 is displaced from the edge and allows for the first housing sheet 20 to be sealed to the second housing sheet 22 (e.g., PVC to PVC). With this method, the filter 10 may be sealed and stamped out (i.e., "tear seal") from the roll stock of the housing sheets and filter medium in a single step. As used herein, the term "tear seal" refers to a method of simultaneously sealing the filter assembly and separating a filter assembly from an adjacent filter assembly. The "tear seal" eliminates the need for a separate cutting step to form the individual filter assemblies, although a separate cutting step can occur instead.

Filters having a single main seal, a main seal and a peripheral seal (sealing together only the plastic housing sheets), two or more main seals with or without a peripheral (i.e. plastic to plastic) seal can be made in accordance with method(s), system(s), apparatus, and/or article(s) of manufacture described herein.

Using a single main seal or a plurality of main seals alone or in combination with a peripheral seal, a filter can be configured within the innermost seal to help ensure even distribution of material in the filter for pump-driven and/or gravity-driven filter implementations. Filter configuration and manufacturing can help reduce cost and provide for streamlined, high volume manufacture.

FIG. 9 depicts a flow diagram of an example method 90 to manufacture filters. At block 91, roll stocks of plastic and/or other flexible film sheeting material are provided to form housing sheets for one or more filters to be manufactured. For example, a process to provide a dual seal for a soft filter can be implemented to seal ten filters at a time across the assembly rollers. At block 93, ports are attached to rolls of the sheeting material. For example, inlet and outlet ports can be punched into and/or otherwise affixed to the sheeting material forming the two sides of the manufactured filter.

At block 95, filtration medium is introduced and/or otherwise brought together between opposed sheets of plastic housing material. At block 97, one or more main seals and an optional peripheral seal are simultaneously formed in the housing sheet and filtration medium material. In some examples, the outer main seal or peripheral seal can be implemented as a tear seal. An example filter can be manufactured using an upper and lower soft shell each having a port and a filtration medium between the upper and lower soft shells and sealed with a main seal, a second seal, and an outer tear seal. Thus, a plurality of filters can be positioned and sealed in a single parallel operation rather than a plurality of serial operations, for example. At block 99, a plurality of individual blood filter assemblies are provided. The manufactured filter assemblies can be separated and/or left together in perforated sets to be separate after shipment, for example. The filter assemblies can be boxed and/or otherwise packaged and shipped to one or more blood collection and/or processing facilitates, for example. The filters can be used during and/or collection of blood to perform leuko-reduction filtering on one or more blood products, for example. Filters can be used for pressure-driven and/or gravity-fed filtering, for example.

For example, as shown in FIG. 8, a series of rolls of filter material can be sandwiched together feeding media into the manufacturing process. Inlet and outlet port holes can be punched in the filter shell material. Then, the port holes can be positioned and sealed to join. Then, the main seal (and optionally other additional seals) can be formed in the material. The seals can be formed in parallel across a width rather than one at a time. In some examples, the port(s) can be positioned in the main seal itself and/or can be formed extending parallel to and/or perpendicular to the filter housing. A second or subsequent seal can be formed through all media, regardless of whether any filtration media is present or not, for example. A tear seal die can be used for easy separation of the formed filters, for example. Alternatively, a die cut can be used for separation. In some examples, the width of the rolled material dictates how many filters can be assembled at one time rather than placement of the filter material.

In some embodiments, the filtration medium can include a porous fiber and/or foam layers. Under low pressure and a slow flow rate, fluid slows down when the filter encounters the filter layer. The fluid gradually wets the filter layer and gently penetrates the layers. In this process, the filter layer can be wet uniformly, and the fluid can pass gradually over all the filter surface area.

Using pressurized or pump drive filtration, the fluid often does not have enough time to wet the surface uniformly because the pressure forces the fluid to penetrate the filter layers. The pressurized fluid quickly wets the filter in a small area (e.g., a pressurized area representing a subset of total available filter area) and causes preferential flow of the fluid through the filter medium. As a consequence, preferential flow reduces the usable filter area due to improper (e.g., uneven) wetting of the filtration medium.

In some embodiments, providing a reflector in conjunction with filtration medium can help avoid creation of a particular pressurized area and can guide the fluid to wet the filter uniformly based on different hole and/or guidance patterns, for example. A fluid reflector or guide can be positioned with respect to a fluid inlet or other input port and/or output port in a filter, for example. Using fluid reflector and/or guide in the filter can help reduce an amount of filtration medium present inside the filter due to more efficient use of the entire filtration medium, for example. A reduction in the amount of filtration medium inside the filter can help reduce cost of filter production, for example. Improved use of filtration material can also result in improved filtering to improve performance of the filter and provide a high quality final product (e.g., leuko-reduced blood product).

In some embodiments, the filtration medium is implemented using a pressure reflecting leuko-reduction filter design to minimize the preferential flow path in the filter so that the performance of the filter can be improved by increased or maximum utilization of the filter surface. The pressure reflecting leuko-reduction filter design can be used with pump driven and/or gravity driven filter systems, for example. For example, a pump driven filter system can generate a pressurized area in the filter resulting in a preferential flow path. Using a reflector design, the pressurized area can be reduced or minimized to improve distribution of fluid in the filter more uniformly. A filter with reflecting/deflecting design can be applied to hard and/or soft housing filters. The reflector size and/or opening design within the reflector can vary depending upon the application, for example. The reflector can be manufactured as hard or soft plastic. The reflector can provide partial or full coverage of a filter. Incorporation of a reflecting filter with an inlet port design can be used to help improve filter performance, for example.

As shown in FIG. 10, an example filter 100 for leuko-reduction of a blood product fluid includes an upper film 101 having an inlet port 103 to accept a fluid, such as a fluid including a blood product. The film 101 can be manufactured as a hard or soft shell film, for example. The film 101 can be manufactured from the same material as that of a blood product container (e.g., bag), for example. The film 101 can include one inlet port 103 or multiple inlet ports 103, for example. The upper film 101 is positioned on top of a reflector 105. The upper film 101 can cover all or part of the reflector 105. The reflector 105 includes one or more openings 107 to allow passage of the fluid from the inlet 103. The reflector 105 directs or targets the flow of the fluid into a filtration medium 109.

The reflector 105 rests on top of the filtration medium 109 including one or more layers of filtering material, such as a depth media formed from melt blown fiber or membrane. The filtration medium 109 accepts and filters the fluid as directed by the opening(s) 107 in the reflector 105. The filtered fluid passes through the filtration medium 109 and exits the filter 100 via an outlet 113 in a film 111. The film 111 can include a plurality of outlet ports 113, for example. A plurality of welding areas 115 seal the upper film 101, reflector 105, filtration material 109, and lower film 111 together, for example, to form the filter 100. The filter 100 can be arranged in a symmetric or asymmetric design, for example. One or more tubes can be connected to the input 103 and output 113 to introduce fluid into and removed filtered fluid from the filter 100.

Figure 11A:
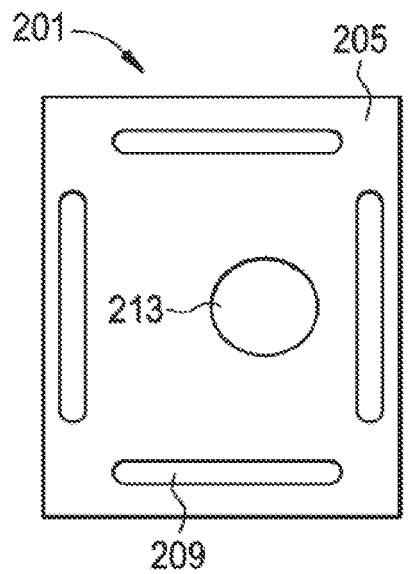
FIGS. 11A-11D depict a plurality of reflector designs for filter assemblies.
Figure 11B:
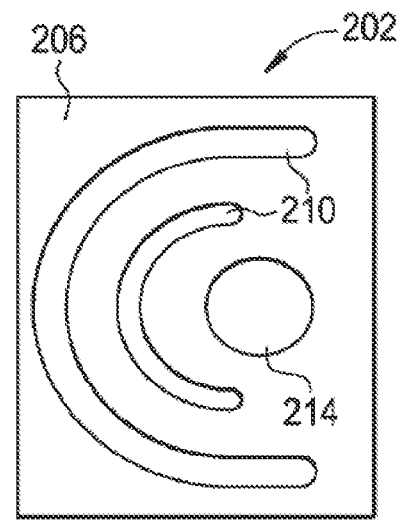
Figure 11C:
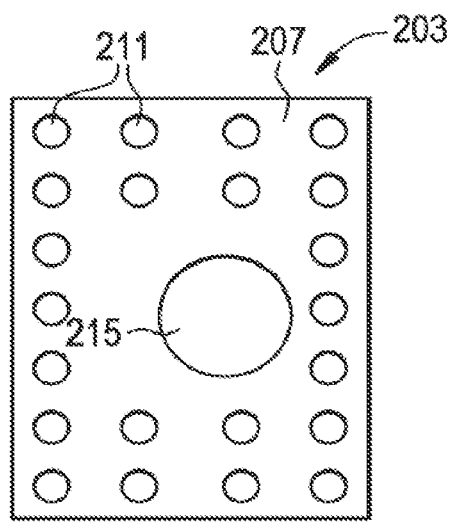
Figure 11D:
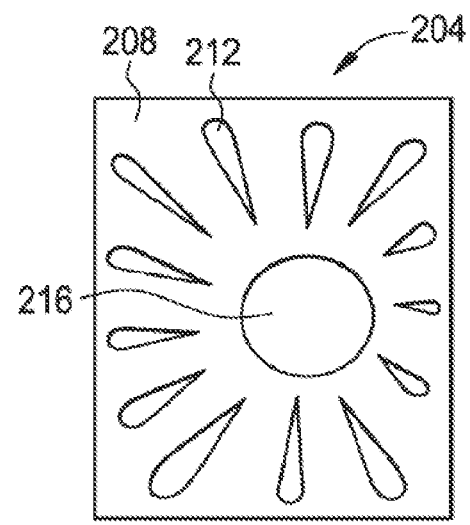

FIGS. 11A-11D depict a plurality of reflector 201-204 designs including a film 205-208 and one or more openings 209-212 arranged in various combinations. The reflectors 201-204 can be used in a pressure filter system, for example, and include openings 209-212 surrounding a high pressure point 213-216 in the reflector film 205-208. FIG. 11(A), for example, a porous area surrounding the high pressure point 213 is defined by a plurality of straight openings 209 in the film 205 arranged in a rectangle or square around the high pressure point 213. FIG. 11(B) shows an example reflector 202 including a plurality of crescent or arced openings 210 in the film 206 surrounding at least one side of the high pressure point 214. In FIG. 11(C), an example reflector 203 includes a plurality of circular or oval openings 211 arranged throughout the film 207 on all sides of the high pressure point 215. The example reflector 204 of FIG. 11(D) includes a plurality of tear drop shaped openings 212 arranged throughout the film 208 on all sides of the high pressure point 216.

Figure 12A:
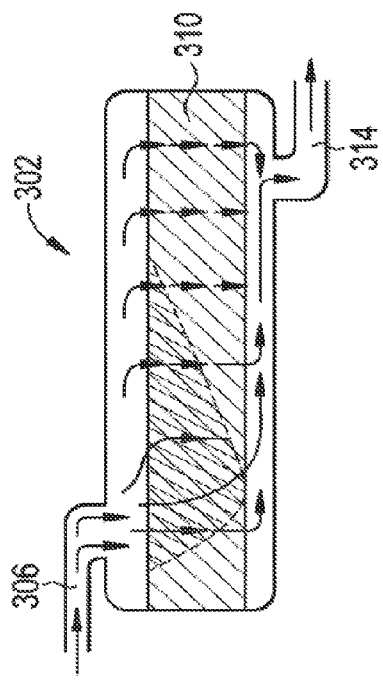
FIGS. 12A-12D illustrate some examples of filter operation.

FIGS. 12A-12D illustrate some examples of filter operation. FIG. 12(A) illustrates an example gravity filter 301 including an inlet 305 introducing fluid to a filter media 309. The fluid flows through the filter media 309 and exits the filter 301 via an outlet 313. Gravity pulls the fluid through the filter media 309 to the outlet 313.

Figure 12B:
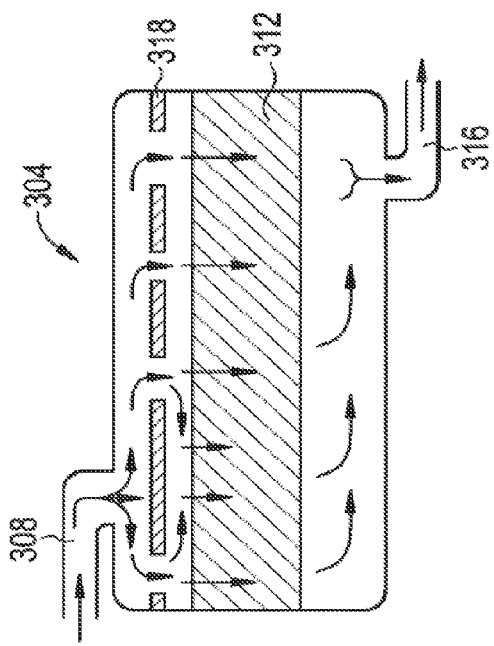

FIG. 12(B) shows an example pressure driven filter 302. The pressure driven filter 302 includes an inlet 306 providing a path for fluid into a filter media 310. Pressure applied (e.g., via a pump) with respect to the filter 302 creates a preferential flow path for the fluid through the filter media 310 to an outlet 314.

Figure 12C:
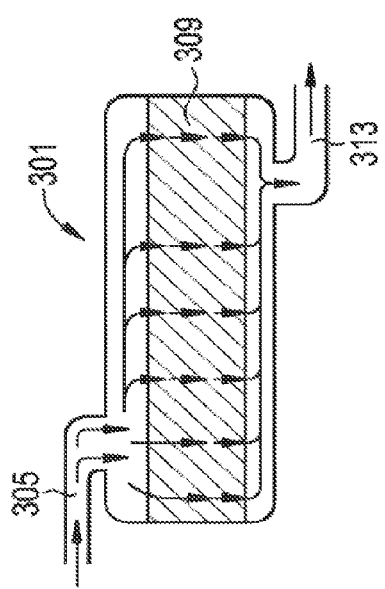

FIG. 12(C) shows an example filter 303 including an enlarged or modified inlet 307 to provide additional space for introduction of a fluid with respect to reflector 317 having one or more openings to distribute and/or route fluid flow from the inlet 307 into a filter media 311. The reflector 317 helps avoid creation of a preferential flow path through the filter media 311 to an outlet 315, such as the pressure driven flow path shown in FIG. 12(B).

Figure 12D:
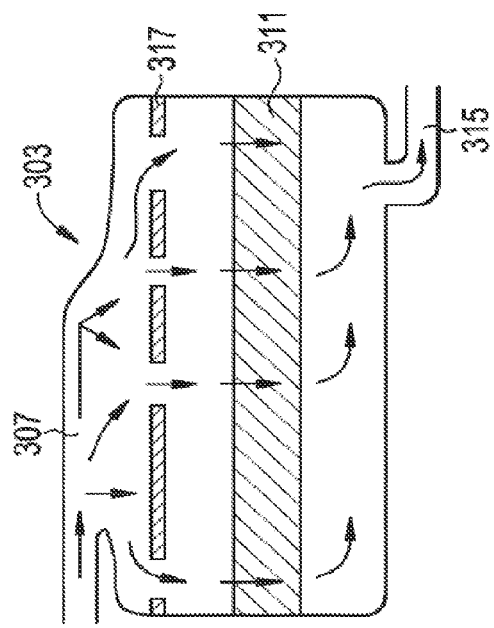

FIG. 12(D) illustrates an example pressure driven filter 304 including an inlet 308 introducing fluid onto a reflector 318 which includes one or more openings to direct the fluid onto a filter media 312 and through the filter media to an outlet 316. The filter media 312, for example, is constructed from a material that resists the fluid, but pressured applied by a pump forces at least a portion of the fluid through the filter media 312. Filtration is related to the surface area of the filter media 312, so improving usage of the available surface area of the filter media 312 improves the quality of the filtration of the fluid. The reflector 318 helps to distribute the fluid across the filter media 312 to increase filter media 312 surface area usage and resulting filtration quality.

Thus, some examples are formed surrounding the filter media and a reflector (if present) with an upper and lower shell formed from a flexible material and sealed with a main seal through the filter media. A second backup seal incorporates the filter media through the particular process. In addition to the second media seal, an outer PVC seal and/or tear seal can be formed in the upper and lower shells of the filter. The outer seal provides additional robustness in conjunction with the first main seal, for example.

Although the present disclosure is described in light of the illustrated embodiments, it is understood that this for the purposes illustration and not limitation. Other applications, modifications or use of the filter assembly may be made without departing from the scope or spirit of this disclosure.

It will be understood that the invention disclosed and defined in this specification extends to all alternative combinations of two or more of the individual features mentioned or evident from the text or drawings. All of these different combinations constitute various alternative aspects of the invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Several embodiments are described above with reference to the drawings. These drawings illustrate certain details of specific embodiments that implement the systems and methods and programs of the present invention. However, describing the invention with drawings should not be construed as imposing on the invention any limitations associated with features shown in the drawings. It will be understood that the invention disclosed and defined in this specification extends to all alternative combinations of two or more of the individual features mentioned or evident from the text or drawings. All of these different combinations constitute various alternative aspects of the invention.

What is claimed is:

1. A method for manufacturing a plurality of filter assemblies comprising:
   providing a first housing sheet and a second housing sheet from housing sheet roll stocks;
   positioning a filtration medium between said first housing sheet and said second housing sheet; and
   applying heat and pressure to form a first seal that commingles the first and second housing sheets along with the filtration medium, a second seal, outboard of the first seal, that commingles at least the first and second housing sheets, and a peripheral seal that commingles the first and second housing sheets outboard of the second seal, wherein
   a periphery of the second seal commingles only the first and second housing sheets,
   a non-seal area is defined between the first seal and the second seal,
   said peripheral seal includes a tear seal enabling separation of a plurality of filter assemblies, and
   the first seal, the second seal, and the peripheral seal of one of said filter assemblies are formed at the same time as the first seal, the second seal, and the peripheral seal of another one of said filter assemblies.

2. The method of claim 1, further comprising positioning and sealing a reflector with respect to the filtration medium, the reflector including at least one opening to direct a flow of fluid from a port onto the filtration medium.

3. The method of claim 2, wherein the reflector comprises a plurality of openings arranged around a point of the filtration medium at which the pressure of a fluid passing through the filtration medium is greater than the pressure of fluid passing through the filtration medium at another point.

4. The method of claim 1, wherein the applying heat and pressure to form the first seal, the second seal, and the peripheral seal comprises using radio frequency sealing to form the first seal, the second seal, and the peripheral seal.

5. The method of claim 1, wherein at least one port is incorporated into the first seal.

6. A method for manufacturing a plurality of filter assemblies comprising:
providing a first housing sheet and a second housing sheet;
associating at least one port with each of the first and second housing sheets;
positioning a filtration medium between said first housing sheet and said second housing sheet;
applying heat and pressure to form a first seal around each port that commingles the first and second housing sheets along with the filtration medium, and a second seal around each port, outboard of each first seal, that commingles at least the first and second housing sheets, and a peripheral seal around each port that commingles the first and second housing sheets outboard of each second seal, wherein
a periphery of each second seal commingles only the first and second housing sheets,
a non-seal area is defined between each first seal and associated second seal, and
the first seal, the second seal, and the peripheral seal of one of said filter assemblies are formed at the same time as the first seal, the second seal, and the peripheral seal of another one of said filter assemblies; and
separating adjacent filter assemblies at the peripheral seals.

7. The method of claim 6, wherein said applying heat and pressure to form the first seal, the second seal, and the peripheral seal and said separating adjacent filter assemblies occur simultaneously.

8. The method of claim 6, wherein said applying heat and pressure to form the first seal, the second seal, and the peripheral seal and said separating adjacent filter assemblies occur sequentially.

9. The method of claim 6, wherein said applying heat and pressure to form the first seal, the second seal, and said peripheral seal comprises using radio frequency sealing to form the first seal, the second seal, and the peripheral seal.

10. The method of claim 6, wherein said separating adjacent filter assemblies includes stamping the peripheral seal to separate adjacent filter assemblies.

11. The method of claim 6, wherein said separating adjacent filter assemblies includes cutting the peripheral seal to separate adjacent filter assemblies.

12. The method of claim 6, further comprising placing a plurality of said filter assemblies into a box or package prior to said separating adjacent filter assemblies.

13. The method of claim 6, further comprising placing a plurality of said filter assemblies into a box or package after said separating adjacent filter assemblies.

14. The method of claim 1, wherein said positioning a filtration medium between said first housing sheet and said second housing sheet includes providing the filtration medium from a filtration medium roll stock.

* * * * *